US012716830B2

(12) United States Patent
Sitko

(10) Patent No.: US 12,716,830 B2
(45) Date of Patent: Aug. 25, 2026

(54) EQUIPMENT FOR MEASURING THE CONTENT OF ORGANIC SUBSTANCES IN WATER EMULSIONS AND SOLUTIONS

(71) Applicant: PBT Works s.r.o., Roznov pod Radhostem (CZ)

(72) Inventor: Vladimir Sitko, Roznov pod Radhostem (CZ)

(73) Assignee: PBT Works s.r.o., Roznov pod Radhostem (CZ)

( * ) Notice: Subject to any disclaimer, the term of this patent is extended or adjusted under 35 U.S.C. 154(b) by 100 days.

(21) Appl. No.: 18/702,420

(22) PCT Filed: Oct. 13, 2022

(86) PCT No.: PCT/IB2022/059821
§ 371 (c)(1),
(2) Date: Apr. 18, 2024

(87) PCT Pub. No.: WO2023/067445
PCT Pub. Date: Apr. 27, 2023

(65) Prior Publication Data
US 2025/0067658 A1 Feb. 27, 2025

(51) Int. Cl.
*G01N 21/15* (2006.01)
*G01N 21/01* (2006.01)
(Continued)

(52) U.S. Cl.
CPC ............. *G01N 21/15* (2013.01); *G01N 21/05* (2013.01); *G01N 21/255* (2013.01); *G01N 21/33* (2013.01);
(Continued)

(58) Field of Classification Search
CPC ...... G01N 21/15; G01N 21/05; G01N 21/255; G01N 21/33; G01N 33/1826;
(Continued)

(56) References Cited

U.S. PATENT DOCUMENTS 9,279,761 B1 * 3/2016 Sternick ................. G01N 21/03
2003/0030005 A1 2/2003 Karki et al.
(Continued)

FOREIGN PATENT DOCUMENTS

EP 2207025 A2 * 7/2010 ............. G01N 21/05

OTHER PUBLICATIONS

Lex D: "In-Line Ratiometric Turbidimeters Are Highly Accurate, Easy to Use", Control Solutions, Pennwell Publishing, Tulsa, OK, US, vol. 66, No. 2, pp. 41-44, XP000361933, ISSN: 1074-2328, Feb. 1993.

(Continued)

*Primary Examiner* — Michelle M Iacoletti
*Assistant Examiner* — Maher Yazback
(74) *Attorney, Agent, or Firm* — Erise IP, P.A.

(57) ABSTRACT

Equipment for measuring the content of organic substances in water emulsions and solutions, characterized by the fact that a sonotrode is placed in the body, near the inlet of the sample into the measuring cell, whereas the body of the instrument contact reductions connected to clamp the cuvette with a seal for mounting the cuvette, a source of UV light with a wavelength of λ1, a source of UV light with a wavelength of λ2, whereas the device is equipped with a broad spectrum turbidimetric photosensor for sensing the signal partially absorbed by the sample, the device being further equipped with a broad-spectrum photosensor to refer signals λ1, λ2 positioned in such a way that the beams from the sources illuminate them directly, perpendicularly to the optical axis of the sources of UV light placed a broad-spectrum photosensor, to detect any reflection from liquid particles of the emulsion or solids.

20 Claims, 2 Drawing Sheets

(51) Int. Cl.
*G01N 21/05* (2006.01)
*G01N 21/25* (2006.01)
*G01N 21/33* (2006.01)
*G01N 33/18* (2006.01)

(52) U.S. Cl.
CPC ..... *G01N 33/1826* (2013.01); *G01N 33/1893* (2013.01); *G01N 2021/0193* (2013.01); *G01N 2021/052* (2013.01); *G01N 2021/154* (2013.01)

(58) Field of Classification Search
CPC ....... G01N 33/1893; G01N 2021/0193; G01N 2021/052; G01N 2021/154; G01N 15/01; G01N 15/075; G01N 2015/0687; G01N 2021/036; G01N 15/06; G01N 21/3151; G01N 21/51; G01N 21/532; G01N 21/01; G01N 21/03
See application file for complete search history.

(56) References Cited

U.S. PATENT DOCUMENTS

| | | | | |
|---|---|---|---|---|
| 2009/0153851 | A1* | 6/2009 | Huemer | G01N 21/05 356/300 |
| 2014/0264096 | A1 | 9/2014 | Brost et al. | |
| 2015/0041682 | A1 | 2/2015 | Cano et al. | |
| 2015/0198521 | A1* | 7/2015 | Moldt | G01N 21/05 356/246 |
| 2020/0122148 | A1* | 4/2020 | Cunningham | B01L 9/06 |
| 2020/0222900 | A1* | 7/2020 | Merchez | G01N 15/10 |
| 2021/0102932 | A1* | 4/2021 | Locklear | G01N 21/75 |
| 2022/0252496 | A1* | 8/2022 | Werk | G01N 1/14 |

OTHER PUBLICATIONS

PCT Patent Application No. PCT/IB2022/059821 International Search Report and Written Opinion dated Jan. 5, 2023.

* cited by examiner

EQUIPMENT FOR MEASURING THE CONTENT OF ORGANIC SUBSTANCES IN WATER EMULSIONS AND SOLUTIONS

RELATED APPLICATION

The present application is a national stage application under 35 U.S.C. § 371 of International Application No. PCT/IB2022/05982, filed Oct. 13, 2022, which claims priority to Czechia Patent Application No. CZ2021-39284U, filed Oct. 19, 2021. The above referenced applications are hereby incorporated by reference.

TECHNICAL FIELDS

The technical solution concerns the equipment to measure the content of liquid organic substances with other organic impurities that are only partially soluble in water, and part of them may fall out of the solution in the form of sticky gel-like or solid particles. Such substances may be water-based emulsion cleaners that dissolve oily or resinous impurities on non-mechanical parts or electronic assemblies, for example, after soldering. This solution can be applied in the technology of measuring properties of water before treatment to better quality or after treatment of polluted water. Also, it can be applied in surface treatment if water-based cleaning technologies are used, followed by rinsing in water, or deionized water, to obtain information about the rinse quality, respectively, further control of the relevant rinsing process.

BACKGROUND ARTS

Measurement of dissolved organic substances in water is a widespread method in the industry. Such measurement—known as Turbidimetry—is used to detect dissolved organic compounds, for example at the inputs of raw water to waterworks for the production of drinking water, or at the outlet of purified water from wastewater treatment stations. The devices designed for this purpose work on the principle of absorption of ultraviolet radiation when passing through a measuring cell, mostly made of quartz glass. Suppose emulsions or solid particles are present in the measured waters. In that case, their presence is measured by reflection from particles or spheres of organic liquid in the emulsion—a method known as nephelometry. These measuring devices require regular inspections and maintenance, especially cleaning the optical part—the cuvette, on the walls of which emulsion droplets may settle or the growth of algae. The problem is also bubbles of gases, which can adhere to the inner surface of the cuvette during degassing of the flowing liquid. Another problem is condensation on the outside surface of the cuvette, caused by a lower sample temperature in an environment with higher humidity, which is common in water processing plants.

There are also existing sensors for measuring small concentrations of organic on a different principle. The principle of operation of those is the measurement of conductivity, subsequent decomposition of all organic substances in the sample by V-UV radiation with a wavelength below 200 μm. The decomposition product is CO2, which is subsequently measured by conductivity detected as the dissociated acid group, and its concentration corresponds to the amount of organic matter in the sample. This principle achieves excellent sensitivity but is not suitable for measuring more polluted water, which occurs in emulsion cleaning processes running with water-based cleaners. It is used only in the field of high-purity water for the production of pharmaceuticals or microelectronics chips.

SUMMARY OF INVENTION

The shortcomings mentioned above regarding the absorption-based method of measuring organic substances in solutions or emulsions are eliminated by equipment according to the submitted technical solution, the essence of which is that the sonotrode of the ultrasonic transducer is placed into the measuring cuvette near the inlet of the liquid sample. To the instrument body, there are attached reductions for clamping the sealed cuvette, a source of UV light with a wavelength of λ1, and a source of UV light with a wavelength of λ2. The device is equipped with a broad-spectrum photodiode for sensing the signal partially absorbed by the sample. The device is also equipped with a broad-spectrum photodiode to reference signals λ1 and λ2 so that the rays from the UV light sources can reach the reference directly without passing the cuvette. Perpendicular to the optical axis of UV light sources, a broad-spectrum photo sensor is placed to detect possible reflection from liquid particles of emulsion or solids. The cuvettes are made of UV-non-absorbing material and are exchangeable or adjustable for a different lengths of the optical path of UV radiation in the sample.

BRIEF DESCRIPTION OF DRAWINGS

The technical solution is further explained in the figures.

DETAILED DESCRIPTION OF THE INVENTION

Figure 1:
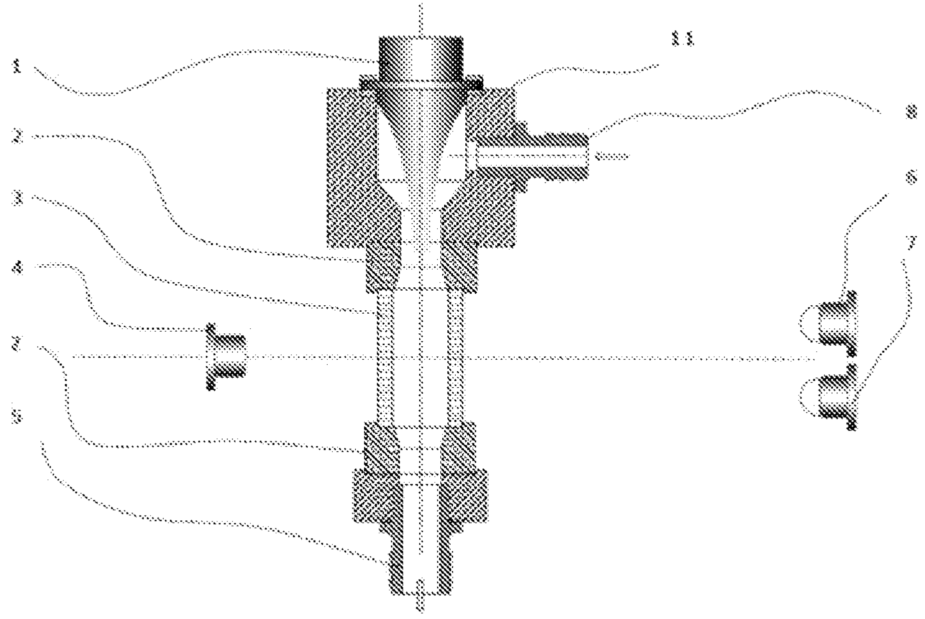
FIG. 1, showing the cross-section guided by the optical axis of the turbidimetric channel.
Figure 2:
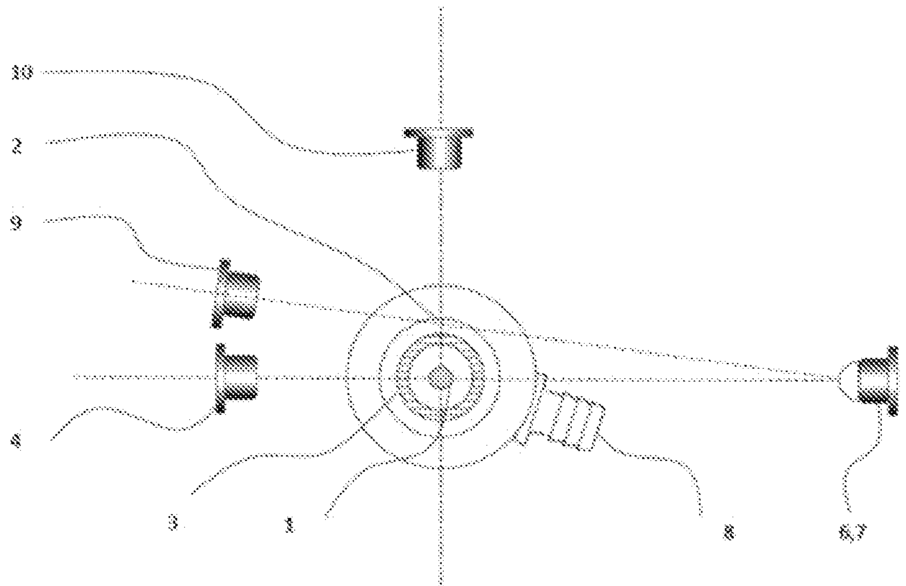
FIG. 2, which is a cross-section guided by a plain of turbidimetric and nephelometric axes of the device.

An example is a device for measuring the concentration of organic substances in the water rinse during cleaning electronic assemblies on printed circuit boards from flux residues after soldering. It consists of body 11 of the device, attached to reductions 2 with a seal for mounting cuvette 3. The cuvette 3 is made from a material that does not absorb UV radiation. Cuvette 3 is exchangeable for cuvettes of a different size of the optical path of the UV beam in the sample. The measured sample of liquid flows through inlet 8 and out through outlet 5. In the body of device 11, there is a cavity for installing ultrasonic sonotrode 1. The sample stream is intensively oscillated by sonotrode 1, and while oscillating, it enters the measuring cuvette 3. The powerful ultrasonic field also extends to cuvette 3 and has two functions. It cleans the walls of transparent cuvette 3 from possible deposits of dissolved residues that fall out of the emulsion and, as insoluble in water but highly sticky, settle on the walls and transparent parts of cuvette 3. At the same time, it increases the emulsification of the sample to the maximum possible level, thus ensuring repeatable concentration reading values.

UV light sources 6, 7 with the appropriate wavelength 21, 22 illuminate the cuvette 3 with a sample. Wide-spectrum photodiode 4 senses a signal partially absorbed by the sample (Turbidimetry). The reference broad-spectrum photodiode 9, which senses the momentary intensity of UV sources, is positioned so that rays from sources 6, 7 illuminate them directly outside cuvette 3. Perpendicularly to the optical axis of the UV light sources 6, 7 and sensor 4, a broad-spectrum photo sensor 10 is placed, which senses any reflection from the liquid droplets of the emulsion or solids. (Nephelometry).

The same configuration can be used to measure raw water before processing into drinking water or treated wastewater after passing through a treatment plant. The measured liquid sample flows through inlet 8 into the cuvette 3 and through outlet 5 from the device. UV light sources 6, 7 with the appropriate wavelength 21 and 22 illuminate the measuring cell 3 with the sample. Cuvette 3 is made of a material that does not absorb the radiation of the corresponding wavelength. The ultrasonic field is applied to the measured sample by the sonotrode 1 directly in front of the measuring cuvette 3. In this application, the primary function of ultrasound is to clean the cuvette from the deposit of organic substances and algae growth.

Broad-spectrum photodiode 4 senses a signal partially absorbed by the sample. (Turbidimetry). The reference broad-spectrum photodiode 9 is positioned so that the rays from sources 6, 7 illuminate them directly outside the cuvette 3. Perpendicularly to the optical axis of the UV light sources 6, 7 and sensor 4, a broad-spectrum photodiode 10 is located, which senses any reflection from liquid droplets of the emulsion or solids for nephelometric measurement.

INDUSTRIAL APPLICABILITY

According to this technical solution, equipment for measuring organic substances in water in the form of genuine solutions or emulsions is usable in the water treatment industry-treatment of raw water to a higher quality or wastewater treatment for monitoring the quality of output water. It can be used to monitor the quality of water rinses in cleaning processes in the electrical and mechanical industries. It applies to all kinds of monitoring organic substances in water where there is a risk of dissolved impurities falling out of the solution or emulsion and deposition on the walls and optical path of the measuring device.

The invention claimed is:

1. A system for measuring a content of organic substances in a sample stream, the system comprising:

- an inlet configured to receive the sample stream,
- wherein the sample stream comprises a cleaning solution utilized to clean a soldered surface of an electronic assembly,
- wherein the organic substances originate from flux residues from soldering the electronic assembly;
- a sonotrode configured to oscillate the sample stream;
- a cuvette removably coupled to a body of the system and configured to allow the sample stream to flow through;
- a plurality of reductions comprising a seal for mounting the cuvette to the body;
- a first UV light source with a first wavelength of λ1 and a second UV light source with a second wavelength of λ2 configured to illuminate the cuvette when the sample stream flows through the cuvette;
- a first broad-spectrum photodiode configured to measure the first wavelength of λ1 and the second wavelength of λ2 partially absorbed by the sample stream;
- a second broad-spectrum photodiode configured to measure the first wavelength of λ1 and the second wavelength of λ2 directly from the first UV light source and the second UV light source;
- a broad-spectrum photo sensor configured to measure a reflection of the first wavelength of λ1 and the second wavelength of λ2 from the sample stream; and
- an outlet configured to allow the sample stream to flow out through.

2. The system of claim 1, wherein the cuvette comprises a UV-non-absorbing material.

3. The system of claim 1, wherein the cuvette is exchangeable to change a length of an optical path of UV radiation in the sample stream.

4. The system of claim 1, wherein the cuvette is adjustable to change a length of an optical path of UV radiation in the sample stream.

5. The system of claim 1, wherein the first broad-spectrum photodiode is positioned along an optic axis of the first UV light source and the second UV light source.

6. The system of claim 5, wherein the broad-spectrum photo sensor is positioned perpendicularly to the optic axis of the first UV light source and the second UV light source.

7. The system of claim 1, wherein the sample stream comprises a water solution or a water emulsion.

8. The system of claim 1, wherein the sonotrode oscillates the sample stream within the cuvette.

9. A method for measuring a content of organic substances in a sample stream, the method comprising:

- collecting the sample stream from a cleaning solution utilized to clean a soldered surface of an electronic assembly,
- wherein the organic substances result from flux residues from soldering the electronic assembly;
- providing a system comprising an inlet, a sonotrode, a body configured to receive the sonotrode, a cuvette, a plurality of reductions comprising a seal, a first UV light source with a first wavelength of λ1, a second UV light source with a second wavelength of Δ2, a first broad-spectrum photodiode, a second broad-spectrum photodiode, a broad-spectrum photo sensor, and an outlet;
- mounting the cuvette to the body via the seal;
- flowing the sample stream through the inlet;
- oscillating the sample stream via the sonotrode;
- flowing the sample stream through the cuvette;
- illuminating the cuvette, while flowing the sample stream through the cuvette, via the first UV light source and the second UV light source;
- measuring the first wavelength of λ1 and the second wavelength of λ2 from the first UV light source and the second UV light source through the cuvette via the first broad-spectrum photodiode;
- measuring the first wavelength of Δ1 and the second wavelength of λ2 directly from the first UV light source and the second UV light source via the second broad-spectrum photodiode;
- measuring a reflection of the first wavelength of λ1 and the second wavelength of λ2 from the sample stream via the broad-spectrum photo sensor; and
- flowing the sample stream through the outlet.

10. The method of claim 9, wherein the oscillating the sample stream occurs within the cuvette.

11. The method of claim 10, wherein the oscillating the sample stream via the sonotrode causes cleaning of a plurality of walls of the cuvette and emulsification of the sample stream.

12. The method of claim 9, wherein the sample stream comprises a water solution or a water emulsion.

13. The method of claim 9, further comprising positioning the first broad-spectrum photodiode along an optic axis of the first UV light source and the second UV light source.

14. The method of claim 9, further comprising positioning the broad-spectrum photo sensor perpendicularly to an optic axis of the first UV light source and the second UV light source.

15. The method of claim 9, further comprising installing the sonotrode into the body of the system proximate the inlet.

16. A system for measuring a content of organic substances in a sample stream, the system comprising:

an inlet configured to receive the sample stream, wherein the sample stream comprises a cleaning solution utilized to clean a soldered surface of an electronic assembly, wherein the organic substances originate from flux residues from soldering the electronic assembly;

a body configured to receive a sonotrode of an ultrasonic transducer proximate the inlet, wherein the sonotrode oscillates the sample stream;

a transparent cuvette configured to allow the sample stream to flow through;

a plurality of reductions coupled to the body and comprising a seal for mounting the transparent cuvette to the body;

a first UV light source with a first wavelength of λ1 and a second UV light source with a second wavelength of λ2 configured to illuminate the transparent cuvette when the sample stream flows through the transparent cuvette;

a first broad-spectrum photodiode positioned on an optical axis of the first UV light source and the second UV light source to measure the first wavelength of λ1 and the second wavelength of λ2 partially absorbed by the sample stream;

a second broad-spectrum photodiode positioned to measure the first wavelength of λ1 and the second wavelength of λ2 directly from the first UV light source and the second UV light source;

a broad-spectrum photo sensor positioned perpendicularly to the optical axis of the first UV light source and the second UV light source to measure a reflection of the first wavelength of λ1 and the second wavelength of λ2 from the sample stream; and an outlet configured to flow the sample stream out of the system.

17. The system of claim 16, wherein the sample stream comprises a water solution or a water emulsion.

18. The system of claim 16, wherein the transparent cuvette comprises a UV-non-absorbing material.

19. The system of claim 16, wherein the transparent cuvette is exchangeable to change a length of an optical path of UV radiation in the sample stream.

20. The system of claim 16, wherein the transparent cuvette is adjustable to change a length of an optical path of UV radiation in the sample stream.

* * * * *